United States Patent
Yang et al.

(10) Patent No.: US 9,266,812 B2
(45) Date of Patent: Feb. 23, 2016

(54) COMB POLYOLEFIN, PROCESS FOR MAKING, AND BLENDS/COMPOSITIONS HAVING SAME

(75) Inventors: Yong Yang, Annandale, NJ (US); Andy Haishung Tsou, Allentown, PA (US); Donna Jean Crowther, Seabrook, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 994 days.

(21) Appl. No.: 13/332,644

(22) Filed: Dec. 21, 2011

(65) Prior Publication Data

US 2013/0165358 A1     Jun. 27, 2013

(51) Int. Cl.
*C10M 107/42* (2006.01)
*C07C 67/343* (2006.01)
*C08F 283/14* (2006.01)
*C08F 299/00* (2006.01)
*C10M 145/14* (2006.01)
*C08G 61/12* (2006.01)

(52) U.S. Cl.
CPC ............. *C07C 67/343* (2013.01); *C08F 283/14* (2013.01); *C08F 299/00* (2013.01); *C10M 145/14* (2013.01); *C08G 61/12* (2013.01); *C08G 2261/419* (2013.01); *C08G 2261/724* (2013.01); *C10M 2205/08* (2013.01); *C10M 2209/084* (2013.01)

(58) Field of Classification Search
CPC .......................... C07C 67/343; C07C 67/3437
See application file for complete search history.

(56) References Cited

U.S. PATENT DOCUMENTS 4,284,835 A    8/1981    Kim et al.
4,980,331 A    12/1990   Hoxmeier et al.
2009/0318647 A1  12/2009  Hagadorn et al.

OTHER PUBLICATIONS

Zaragoza Dorwald, Side Reactions in Organic Synthesis, 2005, WILEY-VCH Verlag GmbH & Co. KGaA, Weinheim, Preface. p. IX.*

Voit, Journal of Polymer Science: Part A: Polymer Chemistry, Hyperbranched Polymers—All Problems Solved after 15 Years of Research?, 2005, vol. 43, 2679-2699.*

Abbas Mudassar and Christian Slugovc, "As low as reasonably achievable catalyst loadings in the cross metathesis of olefins with ethyl acrylate", Tetrahedron Letters (2011), pp. 2560-2562, 52(20), Elsevier Ltd.

J. Scott Parent, Aidan Bodsworth, Saurav S. Sengupta, Marianna Kontopoulou, Bharat I. Chaudhary, Drew Poche, Stephane Cousteaux, "Structure-rheology relationships of long-chain branched polypropylene: Comparative analysis of acrylic and allylic coagent chemistry", Polymer (2009), 50, pp. 85-94, 50(1), Elsevier Ltd.

Hiroshi Tamura, Narinobu Maeda, Rumi Matsumoto, Atsushi Nakayama, Hiroki Hayashi, Kenji Ikushima and Minoru Kuraya, "Synthesis of ester terminated telechelic polymer via ADMET polymerization", Journal of Macromolecular Science, Pure and Applied Chemistry (1999), pp. 1153-1170, A36(9), Marcel Dekker, Inc.

Annabelle F. Newton, Stephen J. Roe, Jean-Christophe Legeay, Pooja Aggarwal, Camille Gignoux, Nicola J. Birch, Robert Nixon, Marie-Lyne Alcarax and Robert A. Stockman, "Two-directional cross-metathesis", Organic & Biomolecular Chemistry, 2009, 7, 2274-2277, 7(11), Royal Society of Chemistry.

H. Rachapudy, G.G. Smith, V.R. Raju and W.W. Graessley, "Properties of Amorphous and Crystallizable Hydrocarbon Polymers. III. Studies of the Hydrogenation of Polybutadiene", Journal of Polymer Science: Polymer Physics Edition, 1979, 17, pp. 1211-1222.

* cited by examiner

*Primary Examiner* — Paul A Zucker
(74) *Attorney, Agent, or Firm* — Robert A. Migliorini

(57) ABSTRACT

Provided is a comb polyolefin. The comb polyolefin has a copolymer of a multifunctional acrylate monomer and a α,ω-diene monomer terminated with a polyolefin substituent. There is also a process for making a comb polyolefin. There is also a polymer backbone. There is also a polyolefin blend. There is also a lubricant composition including the comb polyolefin.

5 Claims, 4 Drawing Sheets

COMB POLYOLEFIN, PROCESS FOR MAKING, AND BLENDS/COMPOSITIONS HAVING SAME

FIELD

The disclosure relates to a comb polyolefin and a process for making. The disclosure further relates to a polymer backbone useful in making the comb polyolefin. There is also a polyolefin blend having the comb polyolefin. There is also a lubricant composition having the comb polyolefin.

BACKGROUND

LDPE (low density polyethylene) exhibits excellent blown film processability but relatively low stiffness and impact toughness. LDPE was made using peroxide initiated radical polymerization of ethylene and contains both short and long chain branches. The excellent processability of LDPE is believed to be due to the presence of long-chain branch structures (dense comb, tree-like, and dendritic structures), although such structures have not been characterized analytically.

HDPE (high density polyethylene) has purely linear PE chains without any long and short chain branches. HDPE exhibits excellent stiffness but poor mechanical toughness and blown film processability.

LLDPE (linear low density polyethylene) contains only short chain branches introduced through the addition of a linear alpha-olefin co-monomer. LLDPE has a heterogeneous composition distribution and exhibits good toughness and moderate stiffness but relatively low blown film processability.

mLLDPE (metallocene catalyst polymerized linear low density polyethylene) has a homogeneous composition distribution containing only short chain branches. mLLDPE exhibits excellent impact toughness and moderate stiffness but very poor blown film processability.

It would be desirable to have an additive for ethylene polymers and for propylene polymers that would enhance extensional hardness, processability, shear thinning, and melt strength. It would also be desirable to have an additive that does not significantly diminish impact toughness and mechanical stiffness of ethylene and propylene polymers.

Polyolefins with a comb-like topology or configuration can provide enhancement of physical properties of ethylene and propylene polymers. However, synthetic methods for comb polyolefins employed in the prior art have proven challenging to carry out, particularly when a tailored structure is desired. It would be desirable to have an effective and efficient process for making comb polyolefins, particularly those with tailored structures.

Polyolefins with a dense comb topology could be used as viscosity modifiers in lubricants. In addition to thickening the lubricant base stock, raising the viscosity index, delivering shear thinning, the comb-like polyolefins could potentially lower the contact friction of lubricants as comb structures are preferred in lubrication applications. It would be desirable to have a comb-like polyolefin that lowered the contact friction of lubricants.

Conventional polypropylenes exhibit only limited melt strength, which has resulted in processing difficulties in blow-molding of bottles and other articles. It would be desirable to have a polyolefin additive that would enhance the melt strength of conventional polypropylenes.

SUMMARY

According to the present disclosure, there is provided a comb polyolefin. The comb polyolefin has a copolymer of a multifunctional acrylate monomer and a $\alpha,\omega$-diene monomer terminated with a polyolefin substituent.

Further according to the present disclosure, there is provided a process for making a comb polyolefin. The process has the steps of a) reacting a multifunctional acrylate monomer with a $\alpha,\omega$-diene monomer to form an alternating acrylate/diene copolymer and b) reacting the alternating acrylate/diene copolymer with a vinyl-terminated polyolefin to form a comb polyolefin.

Further according to the present disclosure, there is provided a polymer backbone. The polymer backbone has a copolymer of a multifunctional acrylate monomer and a $\alpha,\omega$-diene monomer.

Further according to the present disclosure, there is provided an ethylene polymer blend. The blend has a matrix ethylene polymer and 0.1 wt % to 20 wt % of a comb polyolefin based on the weight of the blend. The comb polyolefin includes a copolymer of a $\alpha,\omega$-diene monomer and a multifunctional acrylate monomer terminated with a polyolefin substituent.

Further according to the present disclosure, there is provided a lubricant composition. The composition has 50 wt % or more of a base stock of one or more base oils and 0.1 wt % to 20 wt % of a comb polyolefin based on the weight of the composition.

DETAILED DESCRIPTION

Figure 1:
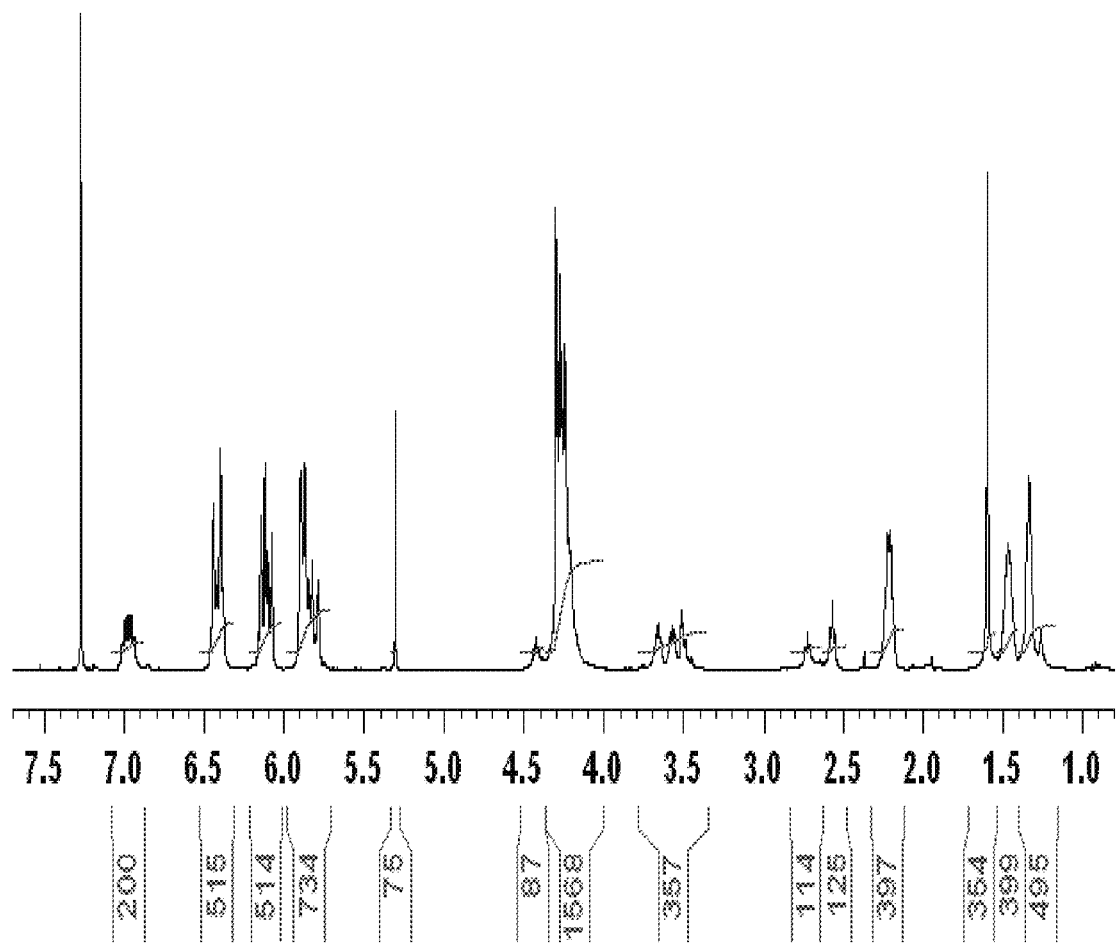
FIG. 1 shows a plot of a $^1$H NMR Spectrum of an embodiment of a comb polyolefin of the present disclosure.

All numerical values within the detailed description and the claims herein are modified by "about" or "approximately" the indicated value, and take into account experimental error and variations that would be expected by a person having ordinary skill in the art.

Comb polyolefins of the present disclosure are obtained from novel reactive backbones derived from alternate copolymers of multi-functional acrylates and $\alpha,\omega$-dienes. The number of reactive sites per chain and the length of polymer backbone can be controlled by the feeding ratio of the multi-functional acrylate monomer to the $\alpha,\omega$-diene monomer. The spacing between two branching points can be controlled by selection of the species of $\alpha,\omega$-diene employed. The crystallinity of the comb polyolefin can be controlled by the crystallizability of the vinyl-terminated polyolefin utilized. The process of the present disclosure affords a high level controllability in comb formation that cannot be attained using conventional synthetic methods.

An embodiment for making the comb polyolefin is illustrated in Scheme 1. It first utilizes cross-metathesis copolymerization of a multi-functional acrylate and a $\alpha,\omega$-diene to synthesize an alternate copolymer with controlled length. Multi-functional acrylates cannot homocouple as a result of the metathesis reaction mechanism. Coupling between the acrylic alkene and the vinyl of diene is thermodynamically favored. Even if the diene homopolymerizes through acyclic diene metathesis polymerization (ADMET) pathway, the acrylate can still be inserted into the double bond in the polymer backbone. This mechanism ensures an alternating copolymer as the major product. The degree of polymerization can be controlled by the monomer feed ratio of the multi-functional acrylate to the α,ω-diene. The multi-functional acrylate is preferably fed with a slight excess to prevent crosslinking. The degree of excess of multi-functional acrylate to the α,ω-diene determines the molecular weight of the reactive backbone (alternating of multifunctional acrylate and diene). A "slight molar excess of multi-functional acrylate to the α,ω-diene" means a ratio of acrylate:diene of from 2:1 to 1:1, more preferably from 1.5:1 to 1.01:1, and even preferably from 1.4:1 to 1.04:1. The unreacted acrylic alkenes in the resulting alternate copolymers can then be available for the second cross metathesis reaction with vinyl-terminated polyolefins yielding a comb structure.

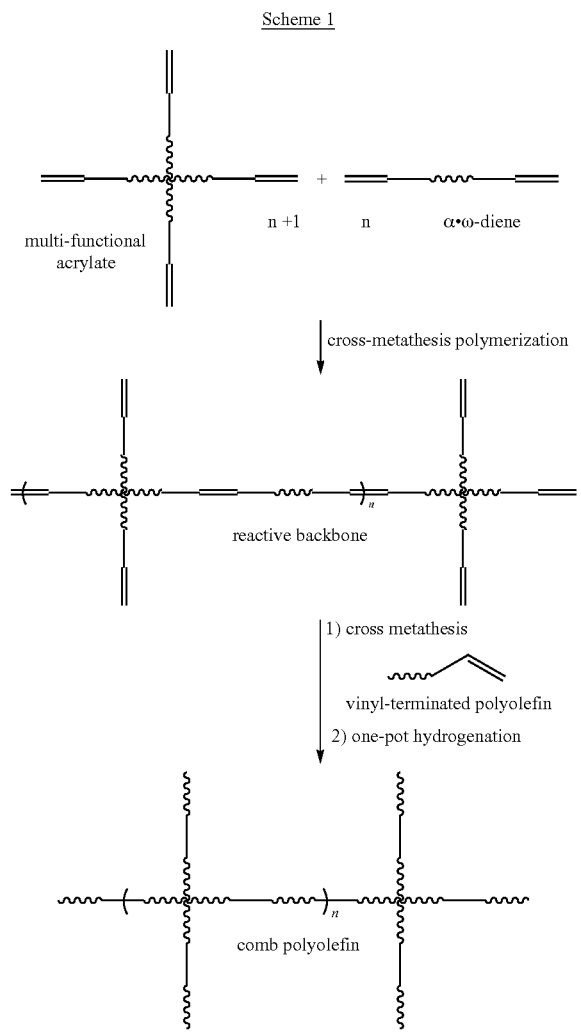

Scheme 1

Useful multi-functional acrylates have 3 or more functionalities, i.e., vinyl terminations, per molecule. The multifunctional acrylate monomer is selected from the group consisting of trimethylolpropane triacrylate (TMPTA), trimethylolpropane ethoxylate triacrylate, glycerol propoxylate (1PO/OH) triacrylate, 1,3,5-triacryloylhexahydro-1,3,5-triazine, tris[2-(acryloyloxy)ethyl]isocyanurate, pentaerythritol tetraacrylate (PETA), di(trimethylol propane) tetraacrylate, dipentaerythritol hexaacrylate (DPEHA), and the like. PETA is a preferred multi-functional acrylate. It is preferred to us a slight molar excess of the acrylates relative to the α,ω-dienes. A "slight molar excess" means a ratio of acrylate:diene of from 2:1 to 1:1, more preferably from 1.5:1 to 1.01:1, and even preferably from 1.4:1 to 1.04:1.

Useful α,ω-dienes have a general formula of $CH_2=CH-CH_2-X-CH_2-CH=CH_2$, wherein X can be any linear molecular structure with an atom number of 0 to 1,000, preferably an atom number 2 to 500, and more preferably an atom number of 4 to 100. Useful linear molecular structures include alkyl groups and ethylene oxide.

The reaction between the multi-functional acrylates and the α,ω-dienes is carried out at a temperature of −40° C. to 120° C., preferably 15° C. to 100° C., and most preferably 20° C. to 80° C. The reaction between the multi-functional acrylates and the α,ω-dienes is preferably carried out at ambient pressure. The reaction between the multi-functional acrylates and the α,ω-dienes is carried out for a time of 1 minute to 170 hours, preferably 10 minutes to 72 hours, and most preferably 30 minutes to 6 hours.

Vinyl-terminated polyolefins can be then grafted onto the remaining pendant acrylate alkenes of the reactive backbone through a cross-metathesis reaction. The vinyl-terminated polyolefin preferably has from 2 to 8 carbons per monomeric unit. Preferred vinyl-terminated polyolefin include polyethylene and polypropylene.

The reaction between the acrylate/diene reactive backbone and the vinyl-terminated polyolefins is carried out at a temperature of −40° C. to 120° C., preferably 15° C. to 100° C., and most preferably 20° C. to 80° C. The reaction between the acrylate/diene reactive backbone and the vinyl-terminated polyolefins is preferably carried out at ambient pressure. The reaction between the acrylate/diene reactive backbone and the vinyl-terminated polyolefins is carried out for a time of 1 minute to 170 hours, preferably 10 minutes to 72 hours, and most preferably 30 minutes to 6 hours.

The comb polyolefin preferably bears 4 or more teeth (the terminated polyolefin chain ends), more preferably 5 to 500 teeth, and most preferably 10 to 100 teeth per polymer chain. The comb polyolefin preferably has an overall molecular weight greater than 5.000, more preferably greater than 15,000, and most preferably greater than 50,000 number average molecular weight. The overall molecular weight can be determined by determining the remaining pendant acrylate alkenes per reactive backbone synthesized and the molecular weight of the vinyl-terminated polyolefin used for grafting.

If necessary, any residual unsaturation in the comb polyolefin can be removed by hydrogenation by any method known in the art. Hydrogenation can be carried out in the process by any known catalysis system, including heterogeneous systems and soluble systems. Soluble systems are disclosed in U.S. Pat. No. 4,284,835 at column 1, line 65 through column 9, line 16 as well as U.S. Pat. No. 4,980,331 at column 3 line 40 through column 6, line 28, all of which is incorporated herein by reference.

Additional teachings to hydrogenation are seen in Rachapudy et al. Journal of Polymer Science: Polymer Physics Edition, Vol. 17, 1211-1222 (1979), which is incorporated herein by reference in its entirety. Table 1 of the article discloses several systems including palladium on various supports (calcium carbonate, but also barium sulfide). The Rachapudy et al. article discloses preparation of homogeneous catalysts and heterogeneous catalysts.

The Rachapudy et al. article discloses a method of preparation of a homogeneous hydrogenation catalyst. The catalyst can be formed by reaction between a metal alkyl and the organic salt of a transition metal. The metal alkyls were n-butyl lithium (in cyclohexane) and triethyl aluminum (in hexane). The metal salts were cobalt and nickel 2-ethyl hexanoates (in hydrocarbon solvents) and platinum and palladium acetyl-acetonates (solids). Hydrogenation was conducted in a 1-liter heavy-wall glass reactor, fitted with a stainless steel flange top and magnetically stirred. A solution of 5 grams of polybutadiene in 500 ml of dry cyclohexane was added, and the reactor was closed and purged with nitrogen. The catalyst complex was prepared separately by adding the transition metal salt to the metal alkyl in cyclohexane under nitrogen. The molar ratio of component metals (alkyl to salt) was generally 3.5/1, the optimum in terms of rate and completeness of hydrogenation. The reactor was heated to 70° C., purged with hydrogen, and the catalyst mixture (usually 0.03 moles of transition metal per mole of double bonds) injected through a rubber septum. Hydrogen pressure was increased to 20 psi (gauge) and the reaction allowed to proceed for approximately 4 hours.

After hydrogenation, the catalyst was decomposed with dilute HCl. The polymer was precipitated with methanol, washed with dilute acid, re-dissolved, re-precipitated and dried under vacuum. Blank experiments with polyethylene in place of polybutadiene confirmed that the washing procedure was sufficient to remove any uncombined catalyst decomposition products.

The Rachapudy et al. article also discloses a method of preparation of a heterogeneous hydrogenation catalyst. A 1-liter high-pressure reactor (Parr Instrument Co.) was used. The catalysts were nickel on kieselguhr (Girdler Co.) and palladium on calcium carbonate (Strem Chemical Co.). Approximately 5 grams of polybutadiene were dissolved in 500 ml of dry cyclohexane, the catalyst was added (approximately 0.01 moles metal/mole of double bonds), and the reactor was purged with hydrogen. The reactor was then pressurized with hydrogen and the temperature raised to the reaction temperature for 3 to 4 hours. For the nickel catalyst, the reaction conditions were 700 psi $H_2$ and 160° C. For palladium, the conditions were 500 psi $H_2$ and 70° C. After reaction the hydrogen was removed and the solution filtered at 70° C. The polymer was precipitated with methanol and dried under vacuum.

The catalysts described herein can be used to hydrogenate hydrocarbons containing saturated carbon bonds. The saturated carbon bonds which may be hydrogenated include olefinic and acetylenic saturated bonds. The process is particularly suitable for the hydrogenation under mild conditions of hydrogenatable organic materials having carbon-to-carbon unsaturation, such as acyclic monoolefins and polyolefins, cyclic monoolefins and polyolefins and mixtures thereof. These materials may be unsubstituted or substituted with additional non-reactive functional groups such as halogens, ether linkages or cyano groups. Exemplary of the types of carbon-to-carbon compounds useful herein are hydrocarbons of 2 to 30 carbon atoms, e.g., olefinic compounds selected from acyclic and cyclic mono-, di- and triolefins. The catalysts of this invention are also suitable for hydrogenating carbon-to-carbon unsaturation in polymeric materials, for example, in removing unsaturation from butadiene polymers and co-polymers such as styrene-butadiene-styrene.

The hydrogenation reaction herein is normally accomplished at a temperature from 40° C. to 160° C. and preferably from 60° C. to 150° C. Different substrates being hydrogenated will require different optimum temperatures, which can be determined by experimentation. The initial hydrogenation pressures may range up to 3,000 psi partial pressure, at least part of which is present due to the hydrogen. Pressures from 1 to 7500 psig are suitable. Preferred pressures are up to 2000 psig, and most preferred pressures are from 100 to 1000 psig are employed. The reactive conditions are determined by the particular choices of reactants and catalysts. The process may be either batch or continuous. In a batch process, reaction times may vary widely, such as between 0.01 second to 10 hours. In a continuous process, reaction times may vary from 0.1 seconds to 120 minutes and preferably from 0.1 second to 10 minutes.

The ratio of catalyst to material being hydrogenated is generally not critical and may vary widely within the scope of the invention. Molar ratios of catalyst to material being hydrogenated between 1:1000 and 10:1 are found to be satisfactory; higher and lower ratios, however, are possible.

If desired, the hydrogenation process may be carried out in the presence of an inert diluent, for example a paraffinic or cycloparaffinic hydrocarbon.

Additional teachings to hydrogenation processes and catalysts are disclosed in U.S. Pat. No. 4,980,331, which is incorporated herein by reference in its entirety.

In general, any of the Group VIII metal compounds known to be useful in the preparation of catalysts for the hydrogenation of ethylenic unsaturation can be used separately or in combination to prepare the catalysts. Suitable compounds, then, include Group VIII metal carboxylates having the formula $(RCOO)_nM$, wherein M is a Group VIII metal, R is a hydrocarbyl radical having from 1 to 50 carbon atoms, preferably from 5 to 30 carbon atoms, and n is a number equal to the valence of the metal M; alkoxides having the formula $(RCO)_nM$, wherein M is again a Group VIII metal, R is a hydrocarbon radical having from 1 to 50 carbon atoms, preferably from 5 to 30 carbon atoms, and n is a number equal to the valence of the metal M; chelates of the metal prepared with beta-ketones, alpha-hydroxycarboxylic acids beta-hydroxycarboxylic acids, beta-hydroxycarbonyl compounds and the like; salts of sulfur-containing acids having the general formula $M(SO_x)_n$ and partial esters thereof; and salts of aliphatic and aromatic sulfonic acids having from 1 to 20 carbon atoms. Preferably, the Group VIII metal will be selected from the group consisting of nickel and cobalt. Most preferably, the Group VIII metal will be nickel. The metal carboxylates useful in preparing the catalyst include Group VIII metal salts of hydrocarbon aliphatic acids, hydrocarbon cycloaliphatic acids and hydrocarbon aromatic acids.

Examples of hydrocarbon aliphatic acids include hexanoic acid, ethylhexanoic acid, heptanoic acid, octanoic acid, nonanoic acid, decanoic acid, dodecanoic acid, myristic acid, palmitic acid, stearic acid, oleic acid, linoleic acid, and rhodinic acid. Examples of hydrocarbon aromatic acids include benzoic acid and alkyl-substituted aromatic acids in which the alkyl substitution has from 1 to 20 carbon atoms. Examples of cycloaliphatic acids include naphthenic acid, cyclohexylcarboxylic acid, and abietic-type resin acids.

Suitable chelating agents which may be combined with various Group VIII metal compounds thereby yielding a Group VIII metal chelate compound useful in the preparation of the catalyst include beta-ketones, alpha-hydroxycarboxylic acids, beta-hydroxy carboxylic acids, and beta-hydroxycarbonyl compounds. Examples of beta-ketones that may be used include acetylacetone, 1,3-hexanedione, 3,5-nonadione, methylacetoacetate, and ethylacetoacetate. Examples of alpha-hydroxycarboxylic acids that may be used include lactic acid, glycolic acid, alpha-hydroxyphenylacetic acid, alpha-hydroxy-alpha-phenylacetic acid, and alpha-hydroxycyclohexylacetic acid. Examples of beta-hydroxycarboxylic acids include salicylic acid, and alkyl-substituted salicyclic acids. Examples of beta-hydroxylcarbonyl compounds that may be used include salicylaldehyde, and θ-hydroxyacetophenone.

The metal alkoxides useful in preparing the catalysts include Group VIII metal alkoxides of hydrocarbon aliphatic alcohols, hydrocarbon cycloaliphatic alcohols and hydrocarbon aromatic alcohols. Examples of hydrocarbon aliphatic alcohols include hexanol, ethylhexanol, heptanol, octanol, nonanol, decanol, and dodecanol. The Group VIII metal salts of sulfur-containing acids and partial esters thereof include Group VIII metal salts of sulfonic acid, sulfuric acid, sulphurous acid, and partial esters thereof. Of the sulfonic acids, aromatic sulfonic acids such as benzene sulfonic acid, p-toluene sulfonic acid, are particularly useful.

In general, any of the alkylalumoxane compounds known to be useful in the preparation of olefin polymerization catalysts may be used in the preparation of the hydrogenation catalyst. Alkylalumoxane compounds useful in preparing the catalyst may, then, be cyclic or linear. Cyclic alkylalumoxanes may be represented by the general formula $(R-Al-O)_m$ while linear alkylalumoxanes may be represented by the general formula $R(R-Al-O)_n AlR_2$. In both of the general formulae R will be an alkyl group having from 1 to 8 carbon atoms such as, for example, methyl, ethyl, propyl, butyl, and pentyl, m is an integer from 3 to 40, and n is an integer from 1 to 40. In a preferred embodiment, R will be methyl, m will be a number from 5 to 20 and n will be a number from 10 to 20. As is well known, alkylalumoxanes may be prepared by reacting an aluminum alkyl with water. Usually the resulting product will be a mixture of both linear and cyclic compounds.

Contacting of the aluminum alkyl and water may be accomplished in several ways. For example, the aluminum alkyl may first be dissolved in a suitable solvent such as toluene or an aliphatic hydrocarbon and the solution then contacted with a similar solvent containing relatively minor amounts of moisture. Alternatively, an aluminum alkyl may be contacted with a hydrated salt, such as hydrated copper sulfate or ferrous sulfate. When this method is used, a hydrated ferrous sulfate is frequently used. According to this method, a dilute solution of aluminum alkyl in a suitable solvent such as toluene is contacted with hydrated ferrous sulfate. In general, 1 mole of hydrated ferrous sulfate will be contacted with from 6 to 7 moles of the aluminum trialkyl. When aluminum trimethyl is the aluminum alkyl actually used, methane will be evolved as conversion of the aluminum alkyl to an alkylalumoxane occurs.

In general, any of the Group Ia, IIa or IIIa metal alkyls or hydrides known to be useful in preparing hydrogenation catalysts in the prior art may be used to prepare the hydrogenation catalyst. In general, the Group Ia, IIa or IIIa metal alkyls will be peralkyls with each alkyl group being the same or different containing from 1 to 8 carbon atoms and the hydrides will be perhydrides although alkylhydrides should be equally useful. Aluminum, magnesium and lithium alkyls and hydrides are particularly useful and these compounds are preferred for use in preparing the catalyst. Aluminum trialkyls are most preferred.

The one or more alkylalumoxanes and the one or more Group Ia, IIa or IIIa metal alkyls or hydrides may be combined and then contacted with the one or more Group VIII metal compounds or the one or more alkylalumoxanes and the one or more Group Ia, IIa or IIIa metal alkyls or hydrides may be sequentially contacted with the one or more Group VIII metal compounds with the proviso that when sequential contacting is used, the one or more alkylalumoxanes will be first contacted with the one or more Group VIII metal compounds. Sequential contacting is preferred. With respect to the contacting step the two different reducing agents; i.e., the alkylalumoxanes and the alkyls or hydrides, might react with the Group VIII metal compound in such a way as to yield different reaction products. The Group Ia, IIa and IIIa metal alkyls and hydrides are a stronger reducing agent than the alkylalumoxanes, and, as a result, if the Group VIII metal is allowed to be completely reduced with a Group Ia, IIa or IIIa metal alkyl or hydride, the alkylalumoxanes might make little or no contribution. If the Group VIII metal is first reduced with one or more alkylalumoxanes however, the reaction product obtained with the alumoxane might be further reduced or otherwise altered by reaction with a Group Ia, IIa or IIIa metal alkyl or hydride. Whether contacting is accomplished concurrently or sequentially, the one or more alkylalumoxanes will be combined with the one or more Group VIII metal compounds at a concentration sufficient to provide an aluminum to Group VIII metal atomic ratio within the range from 1.5:1 to 20:1 and the one or more Group Ia, IIa or IIIa metal alkyls or hydrides will be combined with one or more Group VIII metal compounds at a concentration sufficient to provide a Group Ia, IIa or IIIa metal to Group VII metal atomic ratio within the range from 0.1:1 to 20:1. Contact between the one or more Group VIII compounds and the one or more alkylalumoxanes and the one or more alkyls or hydrides will be accomplished at a temperature within the range from 20° C. and 100° C. Contact will typically be continued for a period of time within the range from 1 to 120 minutes. When sequential contacting is used, each of the two contacting steps will be continued for a period of time within this same range.

In general, the hydrogenation catalyst will be prepared by combining the one or more Group VIII metal compounds with the one or more alkylalumoxanes and the one or more Group Ia, IIa or IIIa metal alkyls or hydrides in a suitable solvent. In general, the solvent used for preparing the catalyst may be anyone of those solvents known in the prior art to be useful as solvents for saturated hydrocarbon polymers. Suitable solvents include aliphatic hydrocarbons, such as hexane, heptane, and octane, cycloaliphatic hydrocarbons such as cyclopentane, and cyclohexane, alkyl-substituted cycloaliphatic hydrocarbons such as methylcyclopentane, methylcyclohexane, and methylcyclooctane, aromatic hydrocarbons such as benzene, hydroaromatic hydrocarbons such as decalin and tetralin, alkyl-substituted aromatic hydrocarbons such as toluene and xylene, halogenated aromatic hydrocarbons such as chlorobenzene, and linear and cyclic ethers such as the various dialkyl ethers, polyethers, particularly diethers, and tetrahydrofuran. Suitable hydrogenation catalysts will usually be prepared by combining the catalyst components in a separate vessel prior to feeding the same to the hydrogenation reactor.

Additional teachings to hydrogenation processes and catalysts are disclosed in U.S. Pat. Nos. 4,284,835 and 4,980,331, both of which are incorporated herein by reference in their entirety.

The comb polymer is preferably substantially saturated. A polymer is deemed saturated if the incidence of unsaturation is less than 10% and preferably less than 5% and most preferably less than 1% according to solution proton NMR.

The comb polyolefins can be used as an additive to increase thickening and viscosity index, deliver shear thinning, and lower contact friction in conventional lubricant base oils and base stocks. The comb polyolefins will typically be present at 0.1 wt % to 20 wt %, more typically from 0.25 wt % to wt %, and most typically 0.5 wt % to 5 wt %.

Useful lubricating base stocks include natural oils and synthetic oils. Groups I, II, III, IV and V are broad categories of base stocks developed and defined by the American Petroleum Institute (API Publication 1509) to create guidelines for lubricant base stocks. Group I base stocks have a viscosity index of 80 to 120 and contain greater than 0.03% sulfur and less than 90% saturates. Group II base stocks have a viscosity index of 80 to 120, and contain less than or equal to 0.03% sulfur and greater than or equal to 90% saturates. Group III stocks have a viscosity index greater than 120 and contain less than or equal to 0.03% sulfur and greater than 90% saturates. Group IV includes polyalphaolefins (PAO). Group V base stock includes base stocks not included in Groups I-IV.

The comb polyolefins can be used as a blend additive to improve processability and/or mechanical properties of conventional polyolefins (compared to polyolefins without the comb polyolefins). Properties that can be improved or enhanced include extensional hardness, shear thinning, and melt strength. Blends of comb polyolefins and conventional polyolefins typically have from 0.1 wt % to 20 wt %, more typically from 0.25 wt % to 10 wt %, and most typically from 0.5 wt % to 5 wt % comb polyolefin based on the total weight of the blend. Conventional polyolefins useful as matrix polymers in the blend include LDPE, LLDPE, mLLDPE, HDPE, VLDPE (very low density polyethylene), iPP (isotactic Polypropylene), RCP (random copolymer of polypropylene), ICP (impact copolymer of polypropylene), propylene elastomers (such as Vistamaxx® from ExxonMobil Chemical, Versify® from The Dow Chemical Company), and polypropylene compound resins (such as Exxtral® from ExxonMobil Chemical).

For instance, the comb polyolefins can be used to increase the extensional hardness and processability in blown polyolefin films, which typically employ LLDPE or mLLDPE. The blown film can be formed by any known process, such as melt extrusion through a mandrel followed by expansion and orientation/hardening with a gas bubble. Improved extensional hardening enhances blown film bubble stability and affords higher production rates and line speeds for blown film. The extensional hardness and processability of blown polyolefin films is preferably increased without substantially diminishing or compromising mechanical performance, optical clarity, and shear viscosity.

For instance, the comb polyolefins can be used to increase the melt strength of polypropylene. Such melt-strengthened polypropylenes are useful in blow-molding operations for the manufacture of bottles and other articles.

The following are examples of the present disclosure and are not to be construed as limiting.

EXAMPLES

Comb polyolefins of the present disclosure were prepared. The comb polyolefins were then characterized by mass spectroscopy (MS), proton nuclear magnetic resonance ($^1$H NMR), and gel permeation chromatography (GPC).

Example 1

A flask was charged with 6 mmol tetraacrylate PETA, 3 mmol 1,9-decadiene and 15 mL dichloromethane (DCM) and stirred to form a solution. A 1 mL DCM solution containing 25 mg (0.03 mmol) of Grubbs $2^{nd}$ generation catalyst was then injected into the stirred monomer solution to form a mixture. The mixture was stirred at 40° C. overnight followed by quenching with several drops of ethyl vinyl ether. Silica gel was added and the mixture was stirred at room temperature for several hours. The silica gel was filtered off and the organic solution was dried. The crude product was confirmed by $^1$H NMR (FIG. 1) as a majority of PETA-diene-PETA "trimer". Mass spectrometry also confirmed the presence of theoretical molecular ions as major peaks (Table 1). This "trimer" (n=1 in Scheme 1) theoretically has 6 unreacted acrylic double bonds in one molecule and can provide 6 branching points per oligomer backbone if all the 6 unreacted acrylic double bonds successfully react with vinyl-terminated polyolefins.

TABLE 1

(The Most Abundant Molecular Ion Peaks Observed in the Mass Spectrometry in FIG. 1)

| Molecular Ion | Calculated | Observed |
| --- | --- | --- |
| $[C_{40}H_{50}O_{16} + H]^+$ | 787.3 | 786.9 |
| $[C_{40}H_{50}O_{16} + NH_4]^+$ | 804.3 | 803.9 |

Example 2

Figure 2:
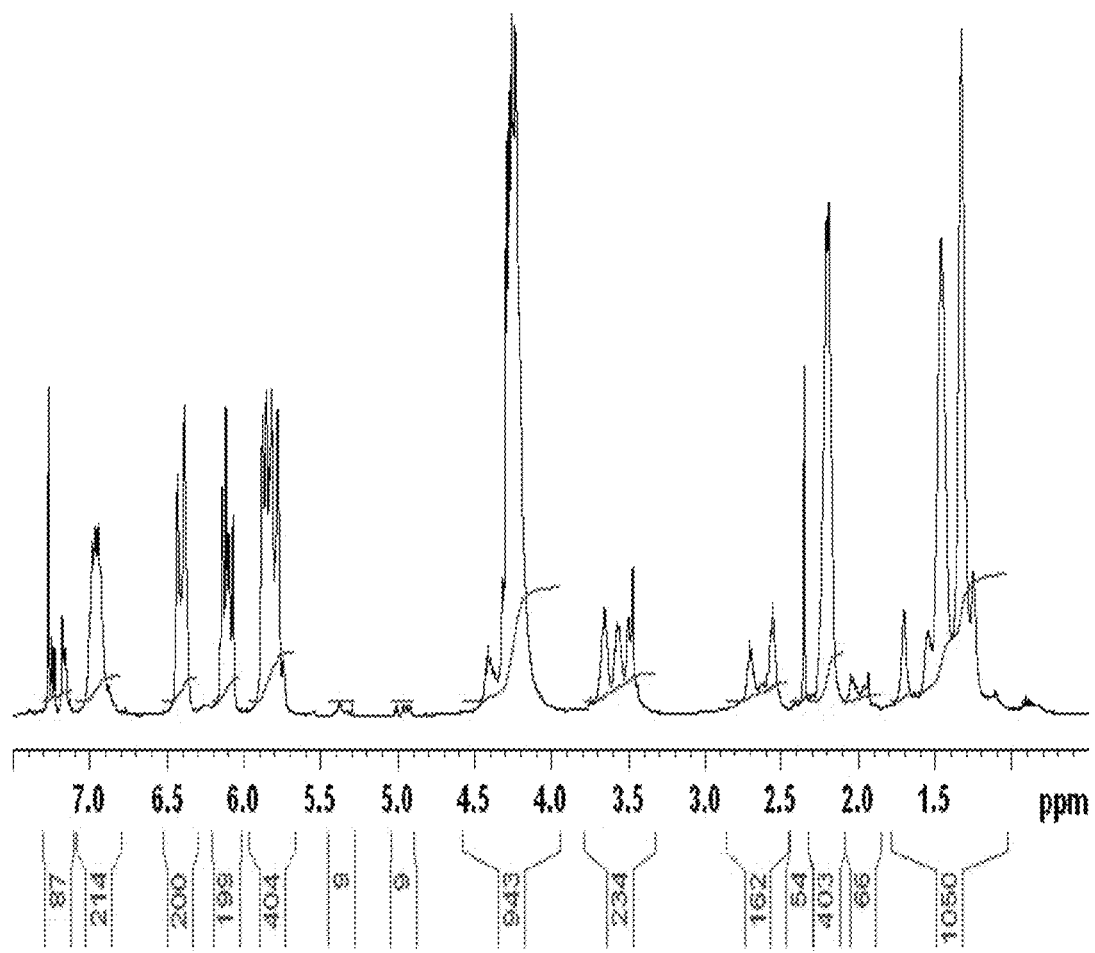
FIG. 2 shows a plot of a $^1$H NMR Spectrum of another embodiment of a comb polyolefin of the present disclosure.

A flask was charged with 1 mmol tetraacrylate PETA, 0.9 mmol 1,9-decadiene and 9.5 mL DCM and stirred to form a solution. A 1 mL DCM solution containing 8.5 mg (0.01 mmol) of Grubbs $2^{nd}$ generation catalyst was then injected into the stirred monomer solution to form a mixture. The mixture was stirred at 40° C. overnight followed by quenching with several drops of ethyl vinyl ether. The mixture was passed through a short silica gel column. The organic solution was dried. The crude product was confirmed by $^1$H NMR (FIG. 2) as a majority of "19mer" (n=9 in Scheme 1). This "19mer" theoretically has 22 unreacted acrylic double bonds in one molecule and can provide 22 branching points per polymer backbone if all the unreacted acrylic double bonds successfully react with vinyl-terminated polyolefins.

Example 3

A flask was charged with 1 mmol tetraacrylate PETA, 0.9 mmol 1,9-decadiene and 9.5 mL DCM and stirred to form a solution. A 1 mL DCM solution containing 8.5 mg (0.01 mmol) Grubbs $2^{nd}$ generation catalyst was then injected into the stirred monomer solution to form a reaction mixture. The reaction mixture was stirred at 40° C. overnight. A small aliquot of the reaction mixture was taken out to analyze the structure of the reactive backbone. To the rest of the reaction mixture, a 4.72 g vinyl-terminated atactic polypropylene (VT-aPP, Mn 2590, 1.82 mmol vinyl) in 20 mL toluene solution was added. A 1 mL toluene solution containing 8.5 mg (0.01 mmol) of Grubbs $2^{nd}$ generation catalyst was then injected. The reaction was stirred at 60° C. under slow nitrogen flow for 60 hours. The reaction was quenched by adding ~0.1 mL ethyl vinyl ether. The quenched reaction mixture was passed through a short silica gel column and the column was washed with a DCM/ethyl acetate (4/1) solvent mixture. The combined organic solution was dried to yield a light brown viscous oil.

Figure 3:
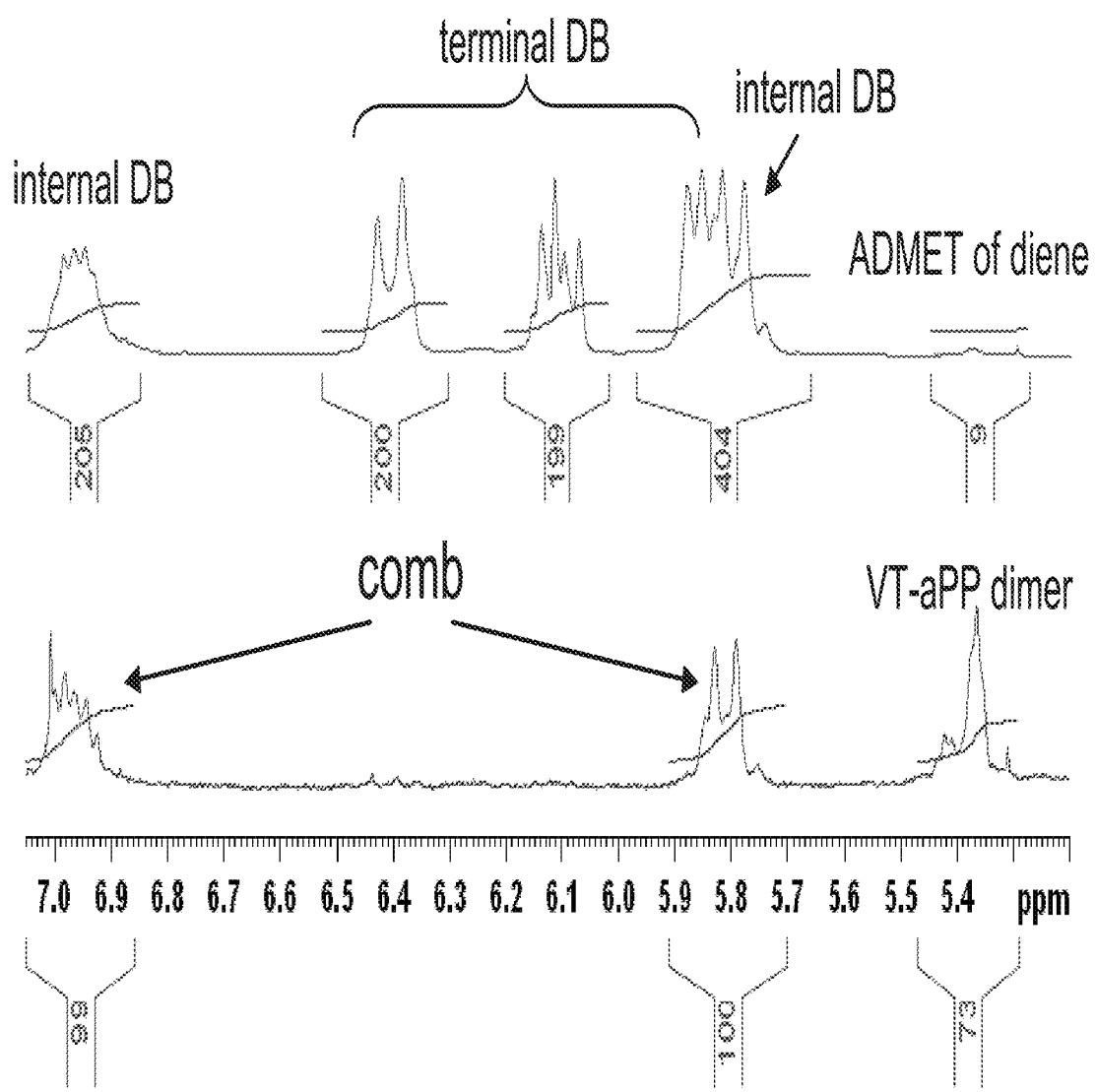
FIG. 3 shows a plot of a $^1$H NMR Spectrum Overlay of another embodiment of a comb polyolefin of the present disclosure.

FIG. 3 shows overlaid partial $^1$H NMR spectra of the reactive backbone (top, green spectrum) and comb aPP (bottom, blue spectrum). It is clearly demonstrated that after the second metathesis reaction, all the terminal double bonds (DBs) disappeared, indicating a complete grafting of the VT-aPP onto the reactive backbone. The new peak around 5.4 ppm in the bottom spectrum indicated the formation of VT-aPP dimer, which may be reduced by using VT-aPP with high vinyl ratio and narrow molecular weight distribution and carefully controlling stoichiometry. The comb aPP showed a bimodal GPC trace with a 91K high molecular weight peak and a 9K low molecular weight peak. The theoretical molecular weight of the comb aPP is 57K and the theoretical molecular weight of the aPP dimer is 5K. Considering the system error in deconvoluting the bimodal GPC trace, the observed and calculated molecular weights roughly matched confirming the formation of the desired comb polyolefin.

Example 4

A flask was charged with 1 mmol tetraacrylate PETA, 0.9 mmol 1,9-decadiene and 50 mL toluene and stirred to form a monomer solution. A 1 mL toluene solution containing 8.5 mg (0.01 mmol) of Grubbs $2^{nd}$ generation catalyst was then injected into the stirred monomer solution to form a reaction mixture. The reaction mixture was stirred at room temperature for 1 hour. Then to the reaction mixture, a 22.884 g vinyl-terminated atactic polypropylene (VT-aPP, Mn 12K, ~2 mmol vinyl) in 80 mL toluene solution was added. The reaction mixture was stirred at room temperature under slow nitrogen flow for 3 days. A small aliquot of the reaction mixture was taken out to analyze the structure of the comb aPP before hydrogenation. The reaction was quenched by adding ~0.5 mL ethyl vinyl ether. Then 3.725 g p-toluenesulfonhydrazide (TSH, mmol) and 3.8 mL tri-n-propylamine (TPA, 20 mmol) were added into the reaction flask. The mixture was heated to reflux for 4 hours followed by precipitation to copious methanol. A hydrogenated comb aPP product was received as a colorless viscous oil. The comb aPP products before and after hydrogenation were checked by $^1$H NMR and their partial NMR spectra were stacked in FIG. 4 for comparison.

Figure 4:
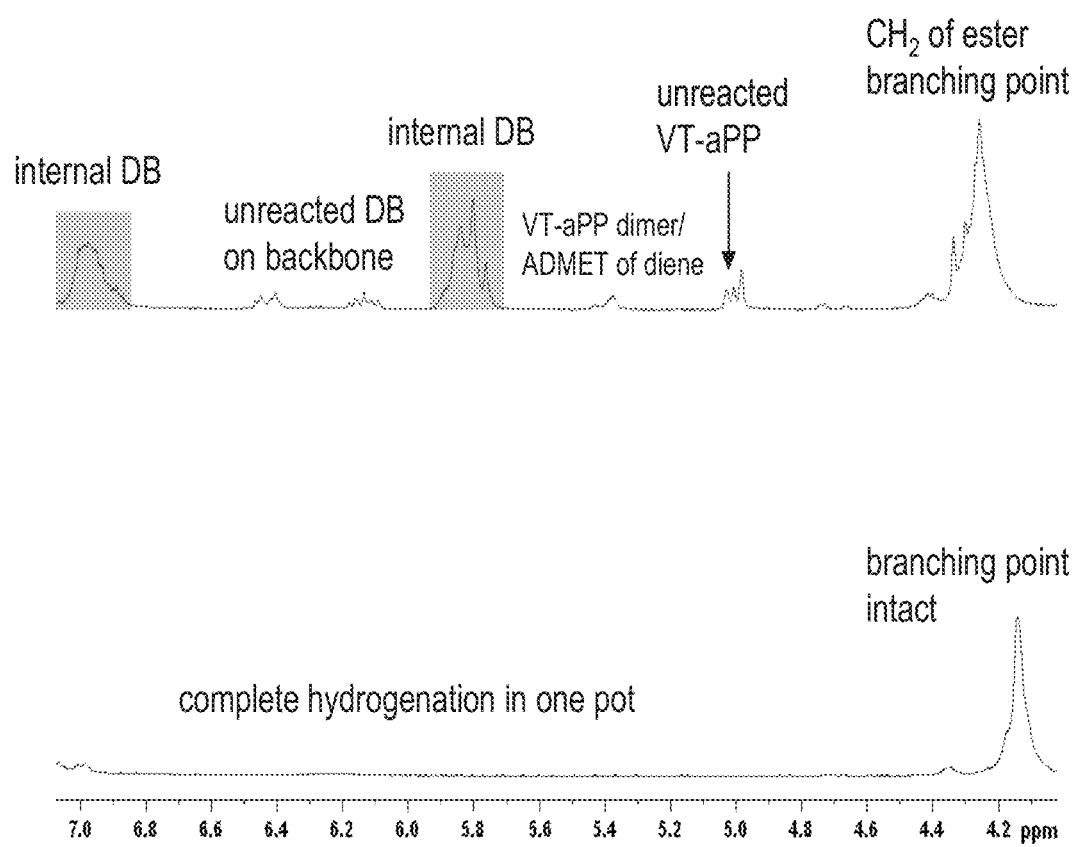
FIG. 4 shows a plot of a $^1$H NMR Spectrum Overlay of another embodiment of a comb polyolefin of the present disclosure.

FIG. 4 shows overlaid partial $^1$H NMR spectra of the comb aPP before hydrogenation (top, red spectrum) and comb aPP after hydrogenation (bottom, blue spectrum). It is clearly demonstrated that after the second metathesis reaction, only a small amount of terminal double bonds (DBs) were left indicating that the grafting of the high molecular weight VT-aPP onto the reactive backbone was at high conversion. The comb aPP product still contained a fair amount of unreacted VT-aPP due to its high molecular weight, broad molecular weight distribution, and low vinyl ratio. After hydrogenation, all the alkene protons disappeared while the $CH_2$ protons next to the ester oxygen still showed up around 4.2 ppm indicating a complete hydrogenation without losing branches. The comb aPP with high molecular weight branches also showed a bimodal GPC trace confirming the formation of the desired comb polyolefin with high molecular weight.

PCT/EP Clauses:

1. A comb polyolefin, comprising a copolymer of a α,ω-diene monomer and a multifunctional acrylate monomer terminated with a polyolefin substituent.

2. The comb polyolefin of clause 1, wherein the comb polyolefin is substantially saturated.

3. The comb polyolefin of either of clauses 1 and 2, wherein the α,ω-diene monomer has the general formula CH2=CH—CH2-X—CH2-CH=CH2, wherein X is a linear molecular structure with an atom number of 0 to 1,000.

4. The comb polyolefin of any of clauses 1 to 3, wherein the multifunctional acrylate monomer is selected from the group consisting of pentaerythritol tetraacrylate, trimethylolpropane triacrylate, trimethylolpropane ethoxylate triacrylate, glycerol propoxylate (1 PO/OH) triacrylate, 1,3,5-triacryloylhexahydro-1,3,5-triazine, tris[2-(acryloyloxy)ethyl]isocyanurate, di(trimethylolpropane) tetraacrylate, dipentaerythritol hexaacrylate.

5. The comb polyolefin of any of clauses 1 to 4, wherein the multifunctional acrylate monomer is in slight molar excess compared to the α,ω-diene monomer.

6. The comb polyolefin of any of clauses 1 to 5, wherein the olefins of the polyolefin of the vinyl-terminated polyolefin have from 2 to 8 carbons per monomeric unit.

7. A process for making a comb polyolefin, comprising:
    a) reacting a multifunctional acrylate monomer with a α,ω-diene monomer to form an alternating acrylate/diene copolymer and
    b) reacting the alternating acrylate/diene copolymer with a vinyl-terminated polyolefin.

8. The process of clause 7, further comprising hydrogenating the comb polyolefin.

9. The process of either of clauses 7 and 8, wherein the α,ω-diene monomer has the general formula CH2=CH—CH2-X—CH2-CH=CH2, wherein X is a linear molecular structure with an atom number of 0 to 1,000.

10. The process of any of clauses 7 to 9, wherein the multifunctional acrylate monomer is selected from the group consisting of pentaerythritol tetraacrylate, trimethylolpropane triacrylate, trimethylolpropane ethoxylate triacrylate, glycerol propoxylate (1PO/OH) triacrylate, 1,3,5-triacryloylhexahydro-1,3,5-triazine, tris[2-(acryloyloxy)ethyl]isocyanurate, di(trimethylolpropane) tetraacrylate, dipentaerythritol hexaacrylate.

11. The process of any of clauses 7 to 10, wherein the multifunctional acrylate monomer is in slight molar excess compared to the α,ω-diene monomer.

12. The process of any of clauses 7 to 11, wherein the olefins of the polyolefin of the vinyl-terminated polyolefin have from 2 to 8 carbons per monomeric unit.

13. A polymer backbone, comprising a copolymer of a multifunctional acrylate monomer and a α,ω-diene monomer.

14. A polyolefin blend, comprising a matrix polyolefin and 0.1 wt % to 20 wt % of a comb polyolefin of clause 1 based on the weight of the blend.

15. A lubricant composition, comprising 50 wt % or more of a base stock of one or more base oils and 0.1 wt % to 20 wt % of the comb polyolefin of claim 1 based on the weight of the composition.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. Likewise, the term "comprising" is considered synonymous with the term "including" for purposes of Australian law.

All patents and patent applications, test procedures (such as ASTM methods, UL methods, and the like), and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains. The disclosure has been described above with reference to numerous embodiments and specific examples. Many variations will suggest themselves to those skilled in this art in light of the above detailed description. All such obvious variations are within the full intended scope of the appended claims.

What is claimed is:

1. A process for making a comb polyolefin, comprising:
    a) reacting a multifunctional acrylate monomer with a α,ω-diene monomer to form an alternating acrylate/diene copolymer and
    b) reacting the alternating acrylate/diene copolymer with a vinyl-terminated polyolefin,
    wherein the α,ω-diene monomer has the general formula CH2=CH—CH2-X—CH2-CH=CH2, wherein X is a linear molecular structure with an atom number of 4 to 100, wherein the linear molecular structure is an alkyl group or ethylene oxide,
    wherein the multifunctional acrylate monomer is selected from the group consisting of pentaerythritol tetraacrylate, trimethylolpropane triacrylate, trimethylolpropane ethoxylate triacrylate, glycerol propoxylate (1PO/OH) triacrylate, 1,3,5-triacryloylhexahydro-1,3,5-triazine, tris[2-(acryloyloxy)ethyl]isocyanurate, di(trimethylolpropane) tetraacrylate, and dipentaerythritol hexaacrylate,
    wherein the multifunctional acrylate monomer is in slight molar excess compared to the α,ω-diene monomer, and
    wherein the olefins of the polyolefin of the vinyl-terminated polyolefin have from 2 to 8 carbons per monomeric unit.

2. The process of claim 1, further comprising hydrogenating the comb polyolefin.

3. The process of claim 1, wherein the α,ω-diene monomer is 1,9-decadiene.

4. The process of claim 1, wherein the multifunctional acrylate monomer is pentaerythritol tetraacrylate.

5. The process of claim 1, wherein the vinyl-terminated polyolefin is selected from the group consisting of vinyl-terminated polyethylene and vinyl-terminated polypropylene.

* * * * *